Figure 1:
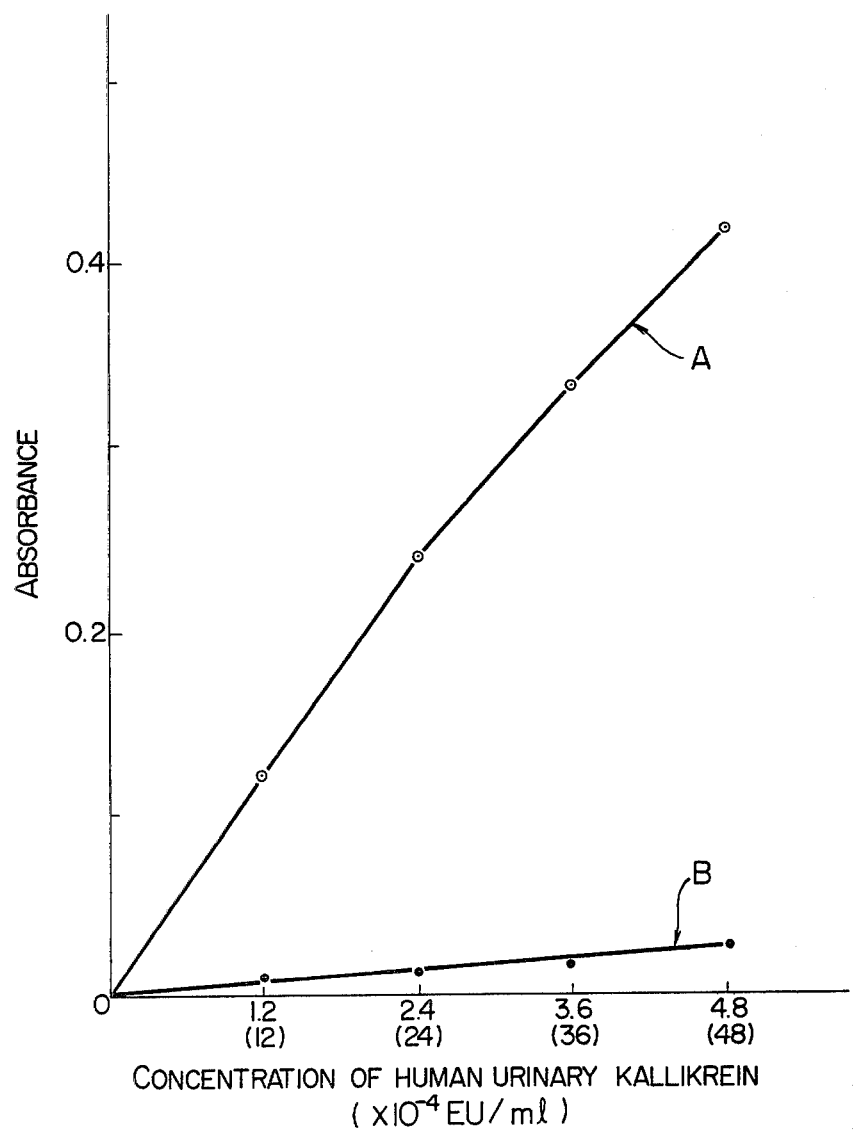

United States Patent [19]  [11] 4,308,202
Fujii et al.  [45] Dec. 29, 1981

[54] PROLYLPHENYLALANYLARGININE DERIVATIVES, PROCESS FOR PRODUCING SAME AND METHOD FOR MEASURING ACTIVITY OF ENZYMES USING SAME

[75] Inventors: Setsuro Fujii, Toyonaka; Mamoru Sugimoto, Chiba; Takashi Yaegashi, Funabashi, all of Japan

[73] Assignee: Torii & Co., Ltd., Tokyo, Japan

[21] Appl. No.: 88,326

[22] Filed: Oct. 25, 1979

[51] Int. Cl.³ .................. C07C 103/52; C12Q 1/56
[52] U.S. Cl. ............................ 260/112.5 R; 435/13
[58] Field of Search .................. 260/112.5 R; 435/13

[56] References Cited

U.S. PATENT DOCUMENTS 3,884,896  5/1975  Blomback et al. ............ 260/112.5 R
3,886,136  5/1975  Claeson et al. ............... 260/112.5 R

FOREIGN PATENT DOCUMENTS 1520261  7/1975  United Kingdom ......... 260/112.5 R

OTHER PUBLICATIONS

Computer Printout, "Tissue Cell", 1978.

Primary Examiner—Delbert R. Phillips

Attorney, Agent, or Firm—Beveridge, DeGrandi, Kline & Lunsford

[57] ABSTRACT

A prolylphenylalanylarginine derivative represented by the formula,

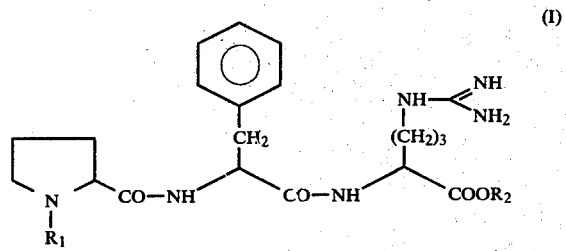

(I)

wherein $R_1$ represents hydrogen or benzoyl; $R_2$ represents naphthyl or 6-bromo-2-naphthyl. The above compound is useful as an excellent substrate for various enzymes, such as trypsin, plasmin, kallikrein, urokinase, Clesterase and the like. Accordingly, the activity of enzymes can be measured by use of said compound as a substrate.

5 Claims, 3 Drawing Figures

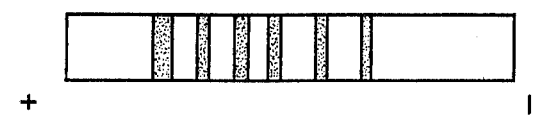
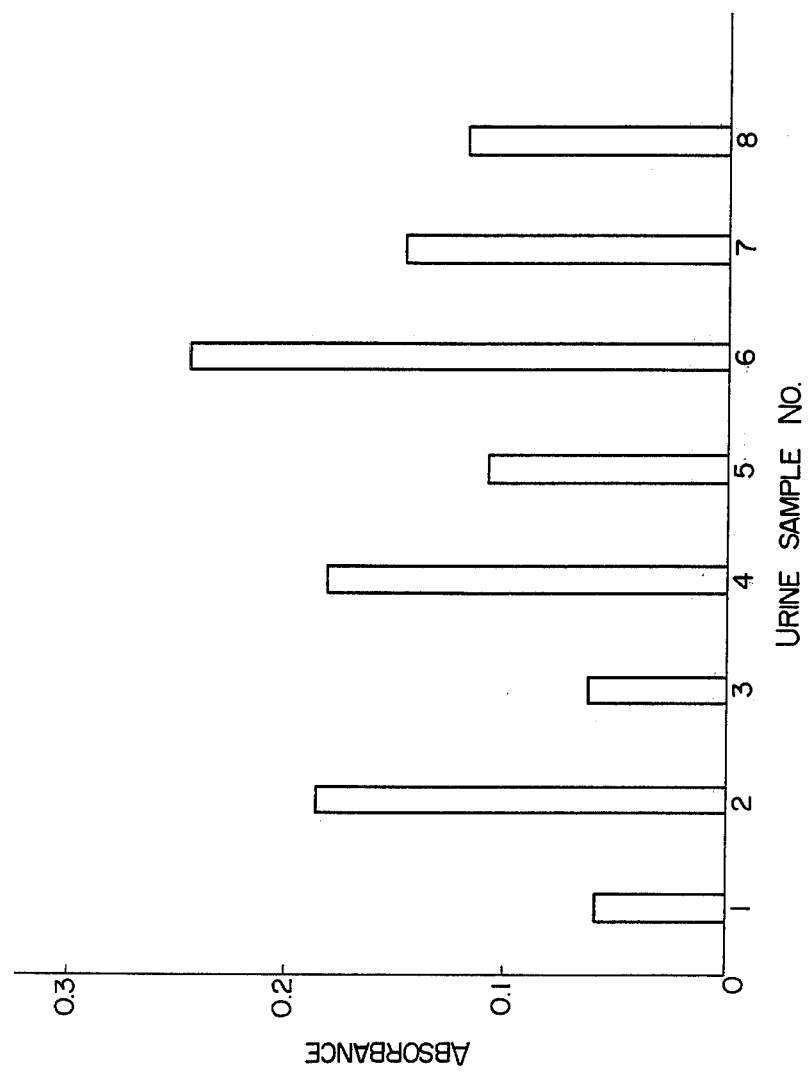

PROLYLPHENYLALANYLARGININE DERIVATIVES, PROCESS FOR PRODUCING SAME AND METHOD FOR MEASURING ACTIVITY OF ENZYMES USING SAME

This invention relates to a prolylphenylalanylarginine derivative, a process for producing the same and a method for measuring the activity of enzymes using the compound as a substrate.

Hitherto, many methods have been known for measuring the activity of enzymes. One of them is a method by which an alkyl ester of an amino acid is contacted as a substrate with an enzyme and the activity of the enzyme is determined from the degree of hydrolysis of the alkyl ester. For example, the well-known Hestrin method is one of the methods. This is a method which comprises contacting an enzyme with an alkyl ester of an amino acid, converting the remaining ester group after a given period of time with hydroxylamine into a hydroxamic acid, allowing it to react with ferric chloride to develop a color, and measuring the color as an absorbance, and determining the enzyme's ability to hydrolyze the ester, namely, the activity of enzyme, from the absorbance.

In addition, there is a method in which paranitroanilide of amino acid is used as a substrate and the ability to hydrolyze the same is used as an index, or the like. In these methods, a considerable amount of an enzyme is required, and when the enzyme concentration is low, or when the enzyme has a low activity, it has been difficult to measure the activity of enzyme.

The present inventors have conducted extensive research on compounds satisfying the following three conditions: they have an affinity to an enzyme, the determination of the amount thereof is easy, and the detection sensitivity thereof is good. Consequently, the inventors have found compounds useful as substrate which are very excellent as to the above conditions as compared with the conventional ones, and a simple method for measuring the activity of enzyme by use of the compounds.

An object of this invention is to provide a novel amino acid derivative which is useful as an excellent substrate for an enzyme.

Another object of this invention is to provide a process for producing the said novel amino acid derivative.

A further object of this invention is to provide a method for measuring the activity of an enzyme by using said novel amino acid derivative as a substrate for the enzyme.

Other objects and advantages of this invention will become apparent from the following description.

According to this invention, there is provided a prolylphenylalanylarginine derivative represented by the formula,

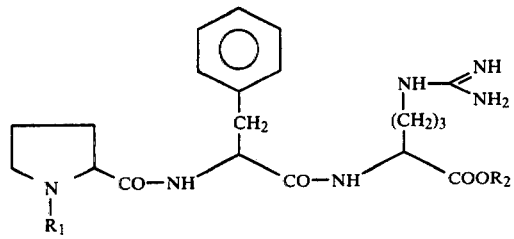

wherein $R_1$ is hydrogen or benzoyl; and $R_2$ is naphthyl or 6-bromo-2-naphthyl.

This invention further provides a process for producing a prolylphenylalanylarginine derivative represented by the formula (I), which comprises subjecting to dehydration-condensation a compound (II) represented by the formula,

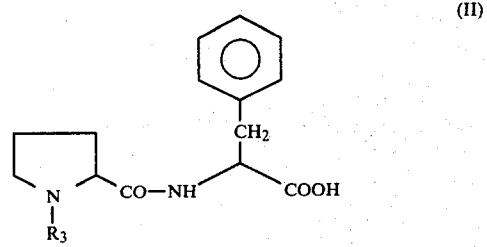

wherein $R_3$ represents benzoyl or an amino-protecting group, and an arginine derivative (III) represented by the formula,

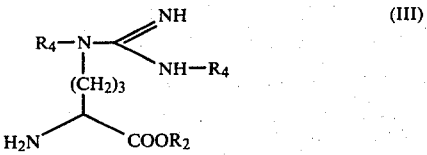

wherein $R_2$ has the same meaning as defined above and $R_4$ represents an amino-protecting group, in a conventional manner to obtain a compound (IV) represented by the formula,

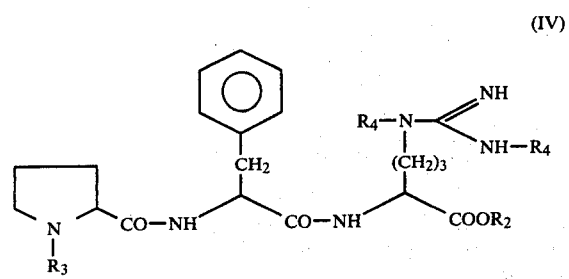

wherein $R_2$, $R_3$ and $R_4$ have the same meanings as defined above, and then removing the amino-protecting group from the compound (IV) in a conventional manner.

According to this invention, there is further provided a method for measuring the activity of an enzyme which comprises contacting a prolylphenylalanylarginine derivative represented by the formula (I) as a substrate with the enzyme.

The starting compound (II) used in the production of the compound (I) of this invention may be any of the compounds stated in Chem. Pharm. Bull., Vol. 20, pp. 664–668, or may be prepared by condensing a compound (V) represented by the formula,

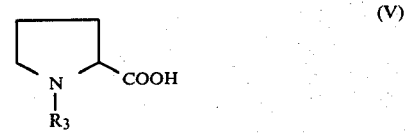

wherein R₃ has the same meaning as defined above, with a compound (VI) represented by the formula,

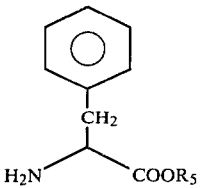
(VI)

wherein R₅ represents alkyl, into an ester (VII) represented by the formula,

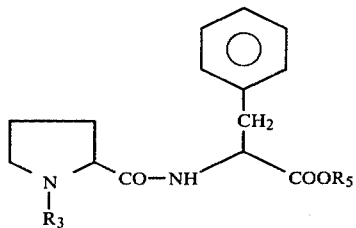
(VII)

wherein R₃ and R₅ have the same meanings as defined above, and then hydrolyzing the ester (VII).

The starting arginine derivative (III) includes $N^G,N^G$-dibenzyloxycarbonyl-L-arginine 1-naphthyl ester trifluoroacetate, $N^G,N^G$-dibenzyloxycarbonyl-L-arginine 6-bromo-2-naphthyl ester trifluoroacetate, and the like, and may be prepared by naphthylating an arginine derivative (III') having a suitable protecting group represented by the formula,

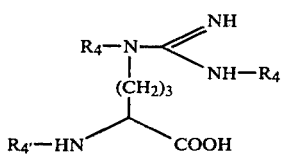
(III')

wherein R₄ has the same meaning as defined above, and R₄' represents an amino-protecting group different from the R₄ group, to form a compound (III") represented the formula,

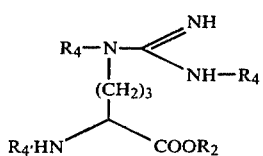
(III")

wherein R₂, R₄ and R₄' have the same meanings as defined above, and then selectively removing only the amino-protecting group in the α-position from the compound (III").

In the production of the compound (IV), the compound (II) and the arginine derivative (III) are dissolved in a suitable solvent, and to the resulting solution is added an activating agent which is usually used, such as dicyclohexylcarbodiimide (DCC), diphenylphosphorylazide (DPPA), an alkyl chlorocarbonate or the like, after which, if necessary, a base such as triethylamine or the like, is added thereto and the resulting mixture is stirred, thereby preparing the compound (IV).

The solvent used includes conventional solvents such as chloroform, dichloromethane, dimethylformamide, tetrahydrofuran and the like as far as the starting materials can be dissolved therein. The reaction temperature may be within the range of 0° to 40° C.

After the completion of the reaction, the compound (IV) can be isolated from the reaction mixture by a conventional treatment. That is to say, when DCC is used as the activating agent, the dicyclohexylurea (DCU) precipitated is removed by filtration, and a suitable extracting solvent such as ethyl acetate is added to the filtrate, after which the extract is washed with an aqueous citric acid solution, saturated aqueous sodium bicarbonate solution or saturated aqueous sodium chloride solution, dried over anhydrous magnesium sulfate, and then evaporated under reduced pressure to remove the solvent to obtain the compound (IV).

The amino-protecting group of the compound (IV) is removed in a conventional manner. That is to say, when the amino-protecting group is benzyloxycarbonyl, the compound (IV) is dissolved in a suitable solvent and a catalyst such as palladium-carbon or the like is added to the resulting solution to remove the protecting group reductively, or the compound (IV) is added to a solution of hydrobromic acid in acetic acid and the hydrobromide of the objective compound precipitated is taken out by filtration, whereby the compound (I) is obtained.

The compound (I) of this invention is useful as an excellent substrate for various enzymes such as trypsin, plasmin, kallikrein, urokinase, Cl-esterase, thrombin and the like. That is to say, when the compound (I) of this invention is contacted with an enzyme, the compound serves as a substrate, and naphthol or 6-bromo-2-naphthol is liberated by hydrolysis with the enzyme after a given period of time, after which the amount of the naphthol or 6-bromo-2-naphthol is measured to determine the activity of the enzyme. The fact that the activity of an enzyme can be measured easily is very important for quantitative analysis of an enzyme preparation, diagonosis by measuring the enzyme pattern in blood, diagonosis by measuring the enzyme concentration in blood or urine, or the like.

When the activity of an enzyme is measured according to the method of this invention, the enzyme is contacted with a given amount of the compound (I) of this invention in a suitable buffer solution, and after a given period of time at a given temperature, the amount of naphthol or 6-bromo-2-naphthol liberated is measured, thereby determining the activity of the enzyme. The buffer solution may be a suitable one having the optimum pH for the enzyme. The reaction may be effected under suitable constant conditions as to temperature and time, though it is preferable to measure the amount of the naphthol or 6-bromo-2-naphthol liberated at a temperature of 25° to 37° C. after 30 min.

The measurement of the amount of naphthol or 6-bromo-2-naphthol may be conducted by any of the known methods, for example, a physicochemical method, such as, gas chromatography, thin layer chromatography, or the like; or a chemical method, such as, ferric chloride reaction, diazo-coupling reaction. Fast Violet B salt (FVB) method, or the like, though a method which comprises adding FVB to the reaction mixture to develop a color and measuring the absorbance by means of a photometer is more preferable in view of simplicity and detection sensitivity.

When the activity of an enzyme is measured using L-prolyl-L-phenylalanyl-L-arginine 1-naphthyl ester as a substrate, the detection sensitivity is higher than when the activity is measured using Nα-benzoyl-L-arginene ethyl ester or Nα-tosyl-L-arginine methyl ester (TAME), which has hitherto been known as a substrate for enzymes, according to the Hestrin method, and in particular, the L-prolyl-L-phenylalanyl-L-arginine 1-naphthyl ester has a detection sensitivity to kallikrein about 160 times that of Nα-benzoyl-L-arginine ethyl ester or Nα-tosyl-L-arginine methyl ester, and about 15 times that of L-prolyl-L-phenylalanyl-L-arginine p-nitroanilide.

The amount of the naphthol or 6-bromo-2-naphthol measured by said method corresponds to the activity or amount of the enzyme.

According to the process of this invention, a change in enzyme concentration in blood or urine due to various diseases can easily be detected. For example, there is a relationship between essential hypertension and the kallikrein concentration in urine of a hypertensive, and it is said that essential hypertension may be diagonosed by measuring the kallikrein concentration. Hitherto, the following methods for measuring the kallikrein concentration in urine have been known:

1. Assay of TAME (Tohoku J. Med., 116 (1975) by Masahide Seino)
2. Bioassay (Tohoku J. Exp. Med., 87 (1965) by Keishi Abe)
3. Radioimmunoassay. These are complicated in operation, and the results obtained are greatly fluctuated. In addition, the methods are expensive and often inconvenient for clinical examination. However, when the compound (I) of this invention is used, the kallikrein concentration in urine can be determined from a small amount of urine by a simple operation.

The method for measuring the activity of an enzyme of this invention can be applied to not only a single enzyme-containing system but also a system containing various systems. That is to say, the measurement of the enzyme pattern in urine or blood has been interesting for diagonosis of disease, but conventional methods have not been so often conducted because of their complexities. However, with this invention, their complexities have been cleared. When, for example, the activity of an enzyme contained in urine is measured, an enzyme pattern in urine which has never been seen has been made possible to see by adding urine on a suitable supporter, separating enzymes therefrom by electrophoresis or the like, immersing the enzymes in an aqueous solution of the compound (I) of this invention for a suitable period of time, and then adding the above-mentioned color developing agent thereto.

This invention is further illustrated below referring to Examples and the accompanying drawings, in which FIG. 1 shows standard curves of the concentration of human urinary kallikrein, FIG. 2 is a graph showing the activity of human urinary kallikrein in human urine, and FIG. 3 shows the enzyme pattern in urine obtained by isoelectrophoresis.

EXAMPLE 1

Production of L-prolyl-L-phenylalanyl-L-arginine 1-naphthyl ester dihydrochloride In 5 ml of dimethylformamide (DMF) were dissolved 396 mg of N-benzyloxycarbonyl-L-prolyl-L-phenylalanine and 682 mg of $N^G,N^G$-dibenzyloxycarbonyl-L-arginine 1-naphthyl ester trifluoroacetate, and to the resulting solution were added 268 mg of dicyclohexylcarbodiimide (DCC), 135 mg of 1-hydroxybenzotriazole (HOBt) and 0.14 ml of triethylamine (TEA) with ice-cooling, after which the mixture was stirred for 3 hrs at the same temperature. The temperature was elevated to room temperature and the mixture was stirred for a further 24 hrs. The crystals of dicyclohexylurea (DCU) precipitated after the reaction were removed by filtration, and ethyl acetate was added to the filtrate, and the mixture was washed with 10% aqueous citric acid solution, saturated sodium bicarbonate solution and saturated sodium chloride solution, dried over anhydrous magnesium sulfate, and thereafter evaporated under reduced pressure to removed the solvent, after which the white powder thus precipitated was collected and recrystallized from chloroform-ether to obtain 600 mg (yield 63%) of N-benzyloxycarbonyl-L-prolyl-L-phenylalanyl-$N^G,N^G$-dibenzyloxycabonyl-L-arginine 1-naphthyl ester, m.p. 164°–167° C.

IR $\nu_{max}^{KBr}$ cm$^{-1}$: 3300, 2925, 1745, 1710, 1630.

NMR $\delta$ ppm (DMSO-d$_6$): 1.5–2.2 (8H, broad), 3.0 (2H, m), 4.0–4.4 (4H, broad), 4.7 (2H, broad), 4.9 (2H, broad), 5.1 (2H×2, s), 5.3 (2H, s), 7.0–8.4 (aromatic protons).

In 10 ml of DMF was dissolved 500 mg of the above ester, and to the resulting solution were added 200 mg of 10% palladium-carbon (Pd-C) and 1.0 g of a hydrochloric acid-dioxane solution (110 mg HCl/g), after which the resulting mixture was stirred at room temperature for 2 hrs while passing hydrogen gas therethrough. After the reaction, the Pd-C was removed by filtration, and 40 ml of anhydrous diethyl ether was added to the filtrate, upon which an oily substance was precipitated. The supernatant was removed by decantation, and 40 ml of anhydrous diethyl ether was added again to the residue and the mixture was stirred to obtain 200 mg (yield 61%) of white powder of L-prolyl-L-phenylalanyl-L-arginine 1-naphthyl ester dihydrochloride, m.p. 87°–90° C. (decomp.).

IR $\nu_{max}^{KBr}$ cm$^{-1}$: 3350, 1750, 1650.

The $N^G,N^G$-dibenzyloxycarbonyl-L-arginine 1-naphthyl ester trifluoroacetate used as the starting material was prepared as follows:

In 30 ml of anhydrous pyridine was dissolved 9.1 g of Nα-4-methoxybenzyloxycarbonyl-$N^G,N^G$-dibenzyloxycarbonyl-L-arginine (Z. Naturf. 20b, 429 (1965), F. Weygand, E. Nintz), and 7.9 g of 1,1'-di-naphthyl sulfite was added to the solution. The resulting mixture was stirred at room temperature for 24 hrs. Ethyl acetate was added to the reaction mixture, and the mixture was washed with 10% citric acid solution, saturated sodium bicarbonate solution and saturated sodium chloride solution in this order, dried over anhydrous magnesium sulfate, and then evaporated under reduced pressure to dryness. Anhydrous diethyl ether was added to the residue to wash the latter, thereby obtaining 9.0 g (yield 82%) of a pale yellow, viscous, oily substance, which was Nα-4-methoxybenzyloxycarbonyl-$N^G,N^G$-dibenzyloxycarbonyl-L-arginine 1-naphthyl ester.

IR $\nu_{max}^{KBr}$ cm$^{-1}$: 3400, 1760, 1720, 1690.

NMR $\delta$ ppm (CDCl$_3$): 1.9 (4H, m), 3.7 (3H, s), 4.1 (2H, m), 4.8 (1H, m), 5.1 (2H×2, s), 5.2 (2H, s), 6.7–8.0 (aromatic protons).

To 8.0 g of the above ester was added 15 ml to trifluoroacetic acid, and the mixture was stirred with ice-cooling for 30 min. After the reaction, the trifluoroacetic acid was removed by evaporation under reduced pressure, and anhydrous diethyl ether was added to the residue to dissolve the latter, after which the resulting solution was allowed to stand. The colorless needle crystals thus precipitated were collected to obtain 4.5 g (yield 61%) of $N^G,N^G$-dibenzyloxycarbonyl-L-arginine 1-naphthyl ester trifluoroacetate, m.p. 149°–151° C.

IR $\nu_{max}^{KBr}$ cm$^{-1}$: 3400, 1760, 1720, 1660.

NMR $\delta$ ppm (CDCl$_3$+DMSO-d$_6$): 2.1 (4H, m), 4.0 (2H, m), 4.5 (1H, m), 5.1 (2H, s), 5.2 (2H, s), 7.1–8.0 (aromatic protons).

EXAMPLE 2

Production of benzoyl-L-prolyl-L-phenylalanyl-L-arginine 1-naphthyl ester hydrochloride In 10 ml of DMF were dissolved 752 mg of benzoyl-L-prolyl-L-phenylalanine and 1.364 g of $N^G,N^G$-dibenzyloxycarbonyl-L-arginine 1-naphthyl ester trifluoroacetate, after which 535 mg of DCC, 270 mg of HOBt and 0.28 ml of TEA were added to the resulting solution with ice-cooling and stirred for 3 hrs. The temperature thereof was thereafter elevated to room temperature, and the mixture was stirred for a further 24 hrs at room temperature. After the reaction, the DCU thus precipitated was removed by filtration, and ethyl acetate was added to the filtrate, and the resulting mixture was washed with 10% citric acid solution, saturated sodium bicarbonate solution and saturated sodium chloride solution in this order, dried over anhydrous magnesium sulfate and then evaporated under reduced pressure to remove the solvent. The residue was recrystallized from ethyl acetate-diethyl ether-n-hexane to obtain 1.20 g (yield 62%) of white powder, m.p. 140°–143° C., which was benzoyl-L-prolyl-L-phenylalanyl-$N^G,N^G$-dibenzyloxycarbonyl-L-arginine 1-naphthyl ester.

IR $\nu_{max}^{KBr}$ cm$^{-1}$: 3400, 3300, 1750, 1720, 1640, 1610.

NMR $\delta$ ppm (CDCl$_3$): 1.6–2.2 (8H, broad), 3.2 (2H, m), 3.5 (2H, m), 4.0 (2H, m), 4.4–5.0 (3H, m), 5.2 (2H, s), 5.3 (2H, s), 7.0–8.0 (aromatic protons).

In 10 ml of DMF was dissolved 962 mg of the above ester, after which 500 mg of 10% Pd-C and 0.5 ml of hydrochloric acid-dioxane solution (98 mg HCl/g) were added to the resulting solution. The resulting mixture was stirred at room temperature for 3 hr while passing hydrogen gas therethrough. After the reaction, the Pd-C was removed by filtration, and 100 ml of anhydrous diethyl ether was added to the filtrate, upon which an oily substance was precipitated. The supernatant was removed by decantation, and anhydrous diethyl ether was added again to the residue, and the mixture was stirred to obtain 600 mg (yield 87%) of white powder, m.p. 80°–90° C. (decomp.), which was benzoyl-L-prolyl-L-phenylalanyl-L-arginine 1-naphthyl ester hydrochloride.

IR $\nu_{max}^{KBr}$ cm$^{-1}$: 3600, 1750, 1650.

The benzoyl-L-prolyl-L-phenylalanine used as the starting material was prepared in the following manner:

In 100 ml of dichloromethane were dissolved 10.7 g of benzoyl-L-proline and 11.5 g of L-phenylalanine ethyl ester hydrochloride, and 15.3 g of DPPA and 15 ml of TEA were added thereto with ice-cooling, after which the mixture was stirred for 24 hrs. The reaction mixture was washed with 10% citric acid solution, saturated sodium bicarbonate solution and saturated sodium chloride solution in this order, then dried over anhydrous magnesium sulfate, and thereafter evaporated under reduced pressure to remove the solvent. The residue was recrystallized from ethyl acetate to obtain 1.20 g (yield 62%) of white powder, m.p. 133°–135° C., which was benzoyl-L-prolyl-L-phenylalanine ethyl ester.

In 100 ml of methanol was dissolved 12.0 g of the above ester, and 45 ml of 1 N sodium hydroxide solution was added thereto, after which the mixture was stirred for 5 hrs. The methanol was removed at a low temperature, and ethyl acetate and distilled water were then added to the residue, after which the resulting mixture was shaken. The aqueous layer was weakly acidified with 10% aqueous hydrochloric acid solution, and the crystalline powder thus precipitated was collected to obtain 10.6 g (yield 95%) of benzoyl-L-prolyl-L-phenylalanine, m.p. 200°–202° C.

IR $\nu_{max}^{KBr}$ cm$^{-1}$: 3375, 1730, 1670.

EXAMPLE 3

Production of benzoyl-L-prolyl-L-phenylalanyl-L-arginine 6-bromo-2-naphthyl ester hydrochloride In 10 ml of DMF were dissolved 376 mg of benzoyl-L-prolyl-L-phenylalanine and 761 mg of $N^G,N^G$-dibenzyloxycarbonyl-L-arginine 6-bromo-2-naphthyl ester trifluoroacetate, after which 267 mg of DCC, 135 mg of HOBt and 0.17 ml of TEA were added thereto with ice-cooling, and the mixture was stirred for 3 hrs, and then at room temperature for a further 24 hrs. The DCU thus precipitated was removed by filtration, and ethyl acetate was added to the filtrate, after which the mixture was washed with 10% citric acid solution, saturated sodium bicarbonate solution and saturated sodium chloride solution in this order, and then dried over anhydrous magnesium sulfate. The solvent was removed by evaporation under reduced pressure, and the residue was recrystallized from ethyl acetate-diethyl ether to obtain 500 mg (yield 50%) of white powder, m.p. 94°–97° C., which was benzoyl-L-prolyl-L-phenylalanyl-$N^G,N^G$-dibenzyloxycarbonyl-L-arginine 6-bromo-2-naphthyl ester.

IR $\nu_{max}^{KBr}$ cm$^{-1}$: 3375, 1750, 1710, 1610.

In 5 ml of DMF was dissolved 0.5 g of the above ester, after which 250 mg of 10% Pd-C, and 250 mg of hydrochloric acid-dioxane solution (98 mg HCl/g) were added thereto. The mixture was stirred at room temperature for 3 hrs while passing hydrogen gas therethrough. After the reaction, the reaction mixture was filtered to remove Pd-C, and 100 ml of anhydrous diethyl ether was added to the filtrate. The white powder thus precipitated was collected to obtain 210 mg (yield 38%) of benzoyl-L-prolyl-L-phenylalanyl-L-arginine 6-bromo-2-naphthyl ester hydrochloride, m.p. 80°–85° C.

IR $\nu_{max}^{KBr}$ cm$^{-1}$: 3350, 1750, 1650.

EXAMPLE 4

Production of L-prolyl-L-phenylalanyl-L-arginine 6-bromo-2-naphthyl ester dihydrochloride In 10 ml of DMF were dissolved 396 mg of N-benzyloxycarbonyl-L-prolyl-L-phenylaranine and 761 mg of $N^G,N^G$-dibenzyloxycarbonyl-L-arginine 6-bromo-2-naphthyl ester trifluoroacerate, after which 267 mg of DCC, 135 mg of HOBt and 0.17 ml of TEA were added thereto with ice-cooling. The mixture was stirred for 3 hrs with ice-cooling and then at room temperature for 24 hrs. The DCU thus precipitated was removed by filtration, and ethyl ester was added to the filtrate. The resulting mixture was washed with 10% citric acid solution, saturated sodium bicarbonate solution and saturated sodium chloride solution in this order, dried over anhydrous magnesium sulfate and then evaporated under reduced pressure to remove the solvent. Diethyl ether was added to the residue, and the resulting mixture was stirred to obtain 610 mg (yield 59.5%) of white powder, m.p. 125°–130° C., which was N-benzyloxycarbonyl-L-prolyl-L-phenylalanyl-$N^G,N^G$-di-benzyloxycarbonyl-L-arginine 6-bromo-2-naphthyl ester.

IR $\nu_{max}^{KBr}$ cm$^{-1}$: 3400, 3300, 1750, 1710, 1650, 1610.

NMR δ ppm (CDCl$_3$): 1.5–2.2 (8H, broad), 3.1 (2H, m), 3.4 (2H, m), 4.0 (3H, m), 4.7 (2H, m), 5.1 (2H, s), 5.2 (2H, s), 5.3 (2H, s), 7.1–8.0 (aromatic protons).

In 5 ml of DMF was dissolved 510 mg of the above ester, after which 250 mg of 10% Pd-C and 440 mg of hydrochloric acid-dioxane solution (98 mg HCl/g) were added thereto, and the mixture was stirred at room temperature for 3 hrs while passing hydrogen gas therethrough. After the reaction, the Pd-C was removed by filtration, and 100 ml of anhydrous diethyl ether was added to the filtrate, and the mixture was allowed to stand with ice-cooling for 24 hrs. The supernatant was removed by decantation, and diethyl ether was again added to the residue, and the mixture was stirred to obtain 230 mg (yield 67%) of white powder, m.p. 80°–84° C., which was L-prolyl-L-phenylalanyl-L-arginine 6-bromo-2-naphthyl ester dihydrochloride.

IR $\nu_{max}^{KBr}$ cm$^{-1}$: 3350, 1750, 1655.

EXAMPLE 5

Measurement of the activity of kallikrein by use of L-prolyl-L-phenylalanyl-L-arginine 1-naphthyl ester dihydrochloride as substrate To 1.7 ml of 50 mM phosphate buffer solution (pH 7.0) were added 0.1 ml of human urinary kallikrein at various concentrations, and 0.2 ml of 1.5 mM solution of L-prolylphenyl-L-alanyl-L-arginine 1-naphthyl ester dihydrochloride dissolved in 0.15% of sodium laurylsulfate solution, after which the mixture was subjected to incubation at 37° C. for 30 min. To the mixture was added 20 microliters of 8% sodium laurysulfate solution and the resulting mixture was cooled with iced water. To the mixture was added 0.2 ml of 1% FVB solution, and the mixture was allowed to stand at 0° C. for 10 min, after which 2 ml of glacial acetic acid was added. The color thus developed was measured as absorbance (505 nm) by means of a spectrophotometer to determine the amount of the naphthol liberated. As a control, the buffer solution free from kallikrein was used. The amount of the naphthol liberated corresponded to the activity of the enzyme.

The results obtained at each kallikrein concentration by the above method are shown in FIG. 1.

When benzoyl-L-prolyl-L-phenylalanyl-L-arginine 1-naphthyl ester hydrochloride was used, the absorbance was measured at 505 nm, and when 6-bromo-2-naphthyl ester was used the absorbance was measured at 530 cm.

Comparative Example 1

Measurement of the activity of kallikrein by use of Nα-tosyl-L-arginine methyl ester hydrochloride as substrate To 0.5 ml of urinary kallikrein were added 0.4 ml of Nα-tosylarginine methyl ester solution (10 micromoles/0.4 ml of 5% DMSO) and 0.1 ml of phosphate buffer (pH 7.4). The mixture was subjected to incubation at 37° C. for 30 min, and 1.5 ml of hydroxylamine solution (a mixture of equal amounts of 2 M NH$_2$OH hydrochloride and 3.5 M NaOH) was added thereto, after which the mixture was allowed to stand at room temperature for 15 min. Thereto were added 1 ml of 18% trichloroacetic acid solution, 1 ml of 4 N hydrochloric acid and 1 ml of 10% ferric chloride solution, and the resulting mixture was stirred thoroughly and then centrifuged at 3,000 r.p.m. for 10 min. The color developed in the supernatant was measured as absorbance (530 nm) by means of a spectrophotometer. The value obtained corresponds to the amount of the substrate remaining unhydrolyzed with kallikrein, and therefore, the activity of the enzyme corresponds to the difference between the value obtained when no enzyme was used (control) and the value obtained after the enzyme reaction.

The results obtained at each kallikrein concentrations in Example 5 and Comparative Example 1 are shown in FIG. 1, from which it can be seen that the method in Example 5 has a sensitivity about 160 times that in the method in Comparative Example 1. In FIG. 1, curve A indicates the standard curve obtained by the method of Example 5 using L-prolyl-L-phenylalanyl-L-arginine 1-naphthyl ester dihydrochloride as a substrate, and curve B indicates the standard curve obtained by the method of Comparative Example 1, in which the numbers in parentheses should be used as the unit of abscissa.

EXAMPLE 6

Measurement of kallikrein in human urine

To 0.1 ml of human urine were added 1.7 ml of 50 mM phosphate buffer solution (pH 7.0) and 0.2 ml of 1.5 mM L-prolyl-L-phenylalanyl-L-arginine 1-naphthyl ester dihydrochloride solution, and the mixture was subjected to incubation at 37° C. for 30 min. The mixture was cooled to 0° C., and 0.2 ml of 1% FVB solution was added thereto, and the resulting mixture was allowed to stand at 0° C. for 10 min, after which 2 ml of glacial acetic acid was added thereto and the color thus developed was measured as absorbance (505 nm) by means of a spectrophotometer, thereby determining the amount of naphthol liberated by hydrolysis with the enzyme. As a control, the same procedure as above was repeated, except that the human urine was used after heat-treated, to measure absorbance, and the difference in absorbance (ΔA) between the two cases was obtained. This difference corresponds to the amount of the kallikrein in human urine. The results of the measurements by the above method are shown in FIG. 2, in which urine samples were obtained from 8 different men (Sample Nos. 1 to 8).

EXAMPLE 7

Measurement of enzyme pattern in urine by isoelectrophoresis

A 4% acrylamide gel column containing 2% Ampholine ® (pH 3.5–5) at a final concentration was prepared by use of a glass tube of 9 mm in inner diameter and 10 cm in length. 2.5 ml of urine was freeze-dried and dissolved in 50 microliters of water to prepare a test specimen. This test specimen was added to the above column and subjected to electrophoresis at 200 V for 4 hrs, after which the gel was taken out, washed with water, immersed in 0.5 M phosphate buffer solution for 5 min, then immersed in 0.25 M phosphate buffer solution (pH 7.0) containing 0.2 micromole of L-prolyl-L-phenylalanyl-L-arginine 1-naphthyl ester and 1% FVB, and thereafter subjected to incubation at 37° C. for 30 min. By the above method, the enzyme pattern in urine can be observed as a pink or violet band. FIG. 3 shows the enzyme pattern obtained when a normal human urine was used.

What is claimed is:

1. A prolylphenylalanylarginine derivative represented by the formula,

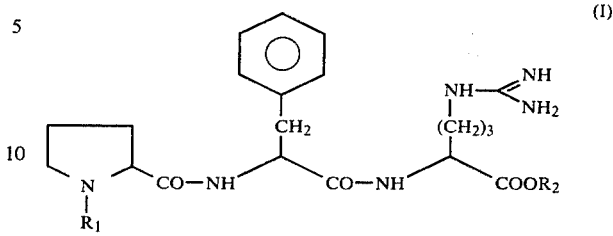

wherein $R_1$ represents hydrogen or benzoyl; and $R_2$ represents naphthyl or 6-bromo-2-naphthyl.

2. L-prolyl-L-phenylalanyl-L-arginine 1-naphthyl ester.

3. Benzoyl-L-prolyl-L-phenylalanyl-L-arginine 1-naphthyl ester.

4. L-prolyl-L-phenylalanyl-L-arginine 6-bromo-2-naphthyl ester.

5. Benzoyl-L-prolyl-L-phenylalanyl-L-arginine 6-bromo-2-naphthyl ester.

* * * * *